United States Patent [19]

Skuballa

[11] Patent Number: 4,912,251

[45] Date of Patent: Mar. 27, 1990

[54] PROCESS FOR MANUFACTURING SYMMETRICAL DIESTERS OF BICYCLO[3.3.0]-OCTANEDIONE DICARBOXYLIC ACID

[75] Inventor: Werner Skuballa, Berlin, Fed. Rep. of Germany

[73] Assignee: Schering Aktiengesellschaft, Berlin and Bergkamen, Fed. Rep. of Germany

[21] Appl. No.: 328,197

[22] PCT Filed: Jul. 1, 1988

[86] PCT No.: PCT/DE88/00414

§ 371 Date: Mar. 17, 1989

§ 102(e) Date: Mar. 17, 1989

[87] PCT Pub. No.: WO89/00555

PCT Pub. Date: Jan. 26, 1989

[30] Foreign Application Priority Data

Jul. 17, 1987 [DE] Fed. Rep. of Germany ....... 3724187

[51] Int. Cl.$^4$ ............................................. C07C 67/343
[52] U.S. Cl. ................................................... 560/119
[58] Field of Search ........................................ 560/119

*Primary Examiner*—Michael L. Shippen
*Attorney, Agent, or Firm*—Millen, White & Zelano

[57] ABSTRACT

The invention concerns a process for manufacturing diesters of bicyclo[3.3.0]-octane dicarboxylic acid having general formula (I), where $R_1$ is a straight-chain or branched-chain alkyl group with 1 to 10 C atoms. The process is charaterized by the fact that a 2-cyclopentenone derivative having general formula (III), where $R_2$ is a hydrogen atom or a straight-chain or branched-chain alkyl group with 1 to 10 C atoms, which can be substituted, if necessary, by a phenyl group, is converted in the presence of a base with a diester of aceton dicarboxylic acid having formula (IV), where $R_1$ has the meaning given above.

9 Claims, No Drawings

PROCESS FOR MANUFACTURING SYMMETRICAL DIESTERS OF BICYCLO[3.3.0]-OCTANEDIONE DICARBOXYLIC ACID

BACKGROUND OF THE INVENTION

The invention relates to a new process for the production of symmetrical bicyclo[3.3.0]octanedione dicarboxylic acid diesters. Optically active 6a-carba-prostacyclin and especially some compounds derived from it have a therapeutic use as stable analogs of the natural prostacyclin (PGI$_2$) [R. C. Nickolsen, M. H. Town, H. Vorbrueggen: Prostacyclin-Analogs, Medicinal Research Reviews, Vol. 5, No. 1, pp. 1–53 (1985)]. The syntheses specified in this recent survey are long and lead partly only to racemic carbacyclins. The syntheses, which lead to carbacyclins in the absolute configuration corresponding to the natural PGI$_2$, are especially expensive. The reason for this is that easily accessible suitable initial materials are achiral and the optical activity must be introduced in the course of the synthesis only in intermediate stages suitable for this purpose.

It is known that symmetrical prochiral dicarboxylic acid diesters of prostacyclin and carbacyclin intermediate stages can be saponified and decarboxylated enantioselectively to the monocarboxylic acid esters in very good yields, if enzymes, especially alpha-chymotrypsin, are used for this purpose (DE 36 38 760.6).

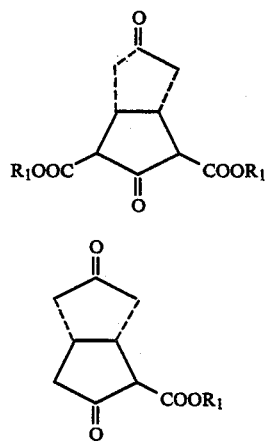

Symmetrical diester I used as initial material for this process is produced, according to literature methods, from 4-acetoxy-2-cyclopenten-1-one and acetone dicarboxylic acid ester [V. Osterthun and E. Winterfeldt, Chem. Ber. 11, 146 (1977) M. Harre, P. Raddatz, R. Walenta and E. Winterfeld, Angew, Chem. 94, 496 (1982)]. In both publications the acetoxy group in the 4-acetoxy-2-cyclopenten-1-one is stressed as the leaving group necessary for the reaction. But the production of 4-acetoxy-2-cyclopenten-1-one proves to be especially expensive and, in addition, uneconomical. Up to now no economical synthesis has been found for this purpose and it has been necessary to resort to the expensive initial materials 4-bromo-2-cyclo-penten-1-one and silver racemate.

SUMMARY OF THE INVENTION

It has now been found that the above-named prochiral, symmetrical dicarboxylic acid diesters I can be produced in very good yields from the easily available 4-hydroxy-2-cyclopenten-1-one [P. G. Baraldi et al., Synthesis 1986, 781; K. Ogura et al., Tetr. Lett. 1976, 759] or 4-tert-butoxy-2-cyclopenten-1-one or 4-cumyloxy-2-cyclopenten-1-one [S. Takano et al., Chem. Pharm. Bull. 34 (8), 3445 (1986); S. Takano et al., Heterocycles 16, 605 (1981)] and acetone dicarboxylic acid esters.

The invention is suitable for the economical production of symmetrical prochiral diesters of general formula I.

Therefore the invention relates to a process for the production of symmetrical bicyclo[3.3.0]octane dicarboxylic acid diesters of general formula I,

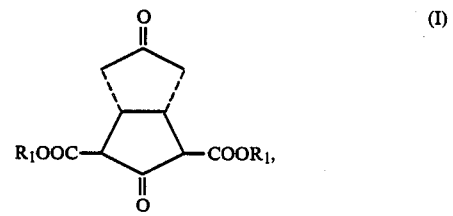

in which R$_1$ represents a straight-chain or branched-chain alkyl group with 1–10 C atoms, characterized in that a 4-hydroxy or 4-alkoxy-2-cyclopenten-1-one of general formula III

in which R$_2$ can be a hydrogen atom or a straight-chain or branched-chain alkyl group with 1–10 C atoms, which optionally can be substituted by a phenyl group, is reacted with acetone dicarboxylic acid diesters of formula IV,

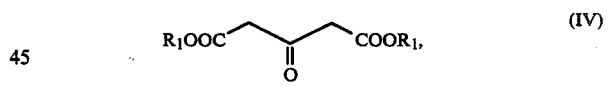

in which R$_1$ has the above-mentioned meaning, in the presence of a base.

Potassium carbonate, sodium carbonate or a tertiary amine such as diisopropylethylamine can, for example, be used as a base for the above process. The reaction is performed at −60° C. to +60° C., preferably 0° to 40° C. Methanol, ethanol, isopropanol, methylene chloride, tetrahydrofuran, among others, can be used as solvents or as solvent mixtures.

The radical methyl, ethyl, propyl, isopropyl, n-butyl, isobutyl, tert-butyl, n-pentyl, isopentyl, neopentyl, n-hexyl, isohexyl, n-heptyl, isohepty, n-octyl, isooctyl, n-nonyl, n-decyl among others are suitable as straight-chain or branched-chain alkyl radical with 1–10 C atoms. The alkyl radicals with 1–6 C atoms are preferred, which can be substituted by a phenyl radical. There can be mentioned, e.g., benzyl, phenethyl, cumyl, etc.

The compounds of formula I produced according to the process of the invention are used for the production of pharmacologically effective prostacyclin derivatives.

The compounds of general formula I can be used for the production of pharmacologically effective carbacylin derivatives [in this connection see R. C. Nickolson, M. N. Town and H. Vorbrueggen. Medicinal Research Review 5, 1 (1985) and P. A. Aristoff in Advances in Prostaglandin, Thromboxane and Leukotriene Research. Vol. 15 (1985))].

Starting from 2,4-bismethoxycarbonyl-bicyclo[3.3.-0]octane-3,7-dione, the active ingredient Iloprost is reached, for example, in a multistage synthesis. Enyntioselective, enzymatic saponification, for example with alpha-chymotrypsin, yields according to DE 36 38 760.6 the optically active monoester IIa.

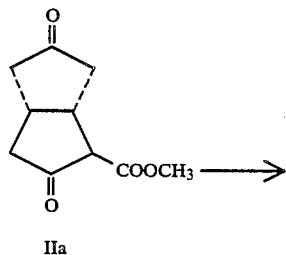

IIa

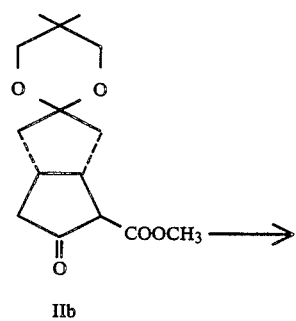

IIb

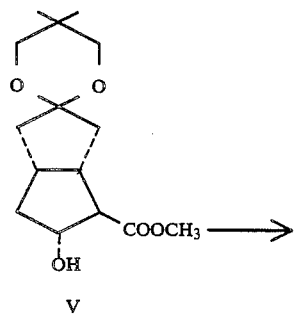

V

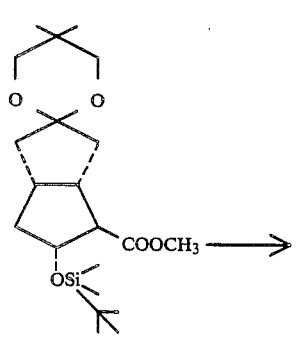

VI

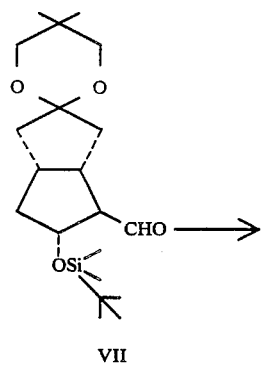

VII

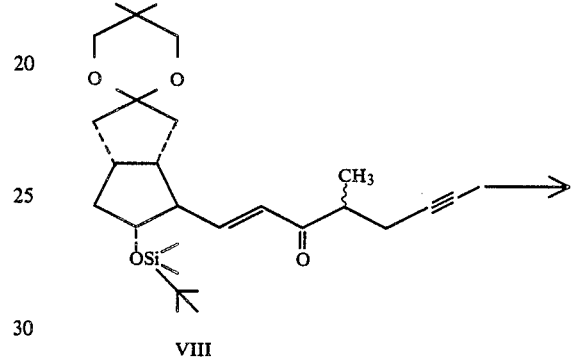

VIII

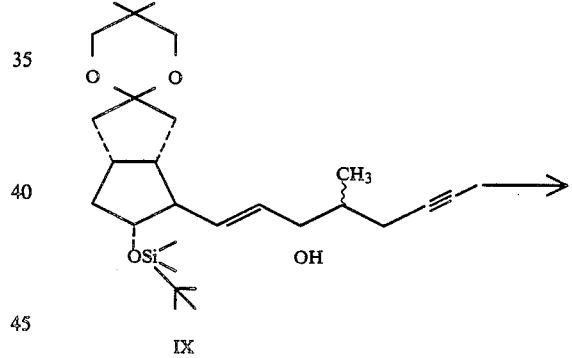

IX

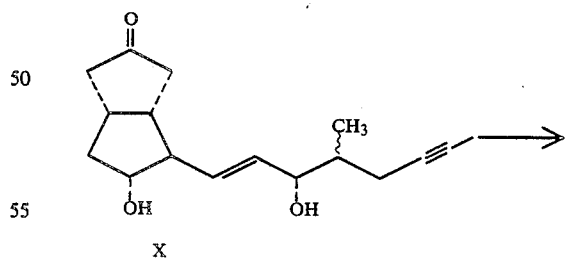

X

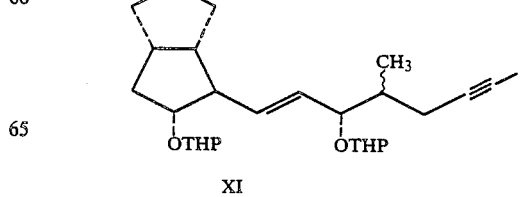

XI

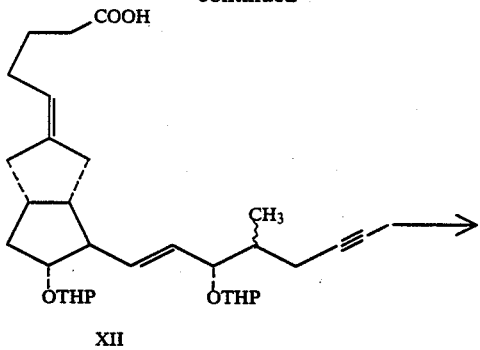

XII

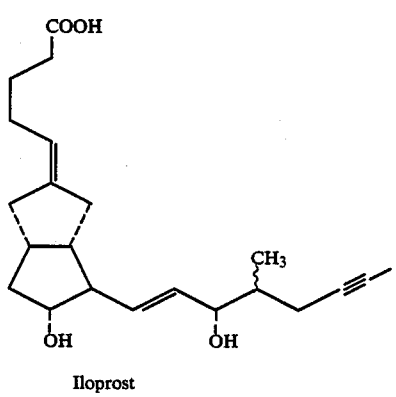

Iloprost

After regioselective protection of the carbonyl group in IIa with formic acid ethyl ester in the presence of 2,2-dimethyl-1,3-diol and a catalytic amount of p-toluenesulfonic acid, IIb is reduced with sodium boron hydride in ethanol to alcohol V. Silyl ether formation (VI) and then reduction with diisobutylaluminum hydride in toluene at −70° C. yields aldehyde VII. which, with 3-methyl-2-oxo-hept-5-in phosphonic acid dimethyl ester and sodium hydride, is condensed to alpha,beta-unsaturated ketone VIII. Reduction of ketone VIII to alcohol IX, then protecting group cleavage to diol X and tetrahydropyranyl ether formation yields ketone XI, which after Wittig reaction with the ylen from 4-carboxybutyltriphenylphosphonium bromide and subsequent protecting group cleavage with aqueous acetic acid is converted into the carbacyclin derivative Iloprost.

The following embodiments serve to explain the process according to the invention but without limiting it.

EXAMPLE 1

2,4-Bismethoxycarbonyl-bicyclo[3.3.0]octane-3,7-dione

A solution of 66 g of 4-tert-butoxy-2-cyclopenten-1-one and 72.1 g of acetone dicarboxylic acid ester in 165 ml of methanol is added at 24° C. to a suspension of 80.1 g of potassium carbonate in 670 ml of methanol and stirred for 23 hours at 25° C. under argon. Then it is acidified with 30% citric acid solution to pH 4, diluted with water and extracted five times with methylene chloride. The organic phase is washed three times with brine, dried on sodium sulfate and concentrated by evaporation in a vacuum. The residue is purified by chromatography on silica gel. 64 g of the title compound as colorless oil is eluted with ethyl acetate/hexane.

IR (CHCl$_3$): 3022, 2962, 1740, 1665, 1624, 1445/cm.

The initial material for the above title compound is produced as follows:

(1a)

4-tert-Butoxy-2-cyclopenten-1-one 90 ml of Jones reagent (chromium trioxide in sulfuric acid) is instilled at −30° C. in a solution of 64.7 g of 4-tert-butoxy-2-cyclopenten-1-ol (produced from cyclopentadiene according to S. Takano et al., Heterocycles, 16, 605 (1981) in 750 ml of acetone and stirred for 20 minutes at −30° C. Then 50 ml of isopropyl alcohol is instilled, diluted with ether and shaken several times with water. It is dried with sodium sulfate and concentrated by evaporation in a vacuum. The residue is used, without further purification, in the condensation reaction according to example 1.

EXAMPLE 2

2,4-Bismethoxycarbonyl-bicyclo[3.3.0]octane-3,7-dione

A solution of 13.7 g of 4-hydroxy-2-cyclopent-1-one (for example, produced from 2-methylfuran according to v. Clauson-Kas et al., Acta chem. scand. 1947, 619 or Synthesis 1986, 781) and 25.36 ml of acetone dicarboxylic acid diethyl ester in 42 ml of ethanol is instilled in a stirred solution of 27 g of potassium carbonate in 116 ml of ethanol at 0° C. under argon, stirred for 1 hour at 0° C. and 24 hours at 25° C. It is concentrated by evaporation in a vacuum, 200 ml of water is added, it is acidified with 20% citric acid solution to pH 4, extracted with methylene chloride and the organic extract is washed with brine. It is dried on magnesium sulfate and concentrated by evaporation in a vacuum. The residue is purified by chromatography on silica gel. 28 g of the title compound as colorless oil is eluted with ethyl acetate/hexane.

IR (CHCl$_3$): 3021, 2960, 1740, 1665, 1624, 1446/cm.

EXAMPLE 3

2,4-Bismethoxycarbonyl-bicyclo[3.3.0]octane-3,7-dione

A solution of 1 g of 4-cumyloxy-2-cyclopenten-1-one an 0.83 g of acetone dicarboxylic acid ester in 1.9 ml of methanol is added to a suspension of 900 mg of potassium carbonate in 7.5 ml of methanol at 25° C. and stirred for 24 hours at 25° C. under argon. It is then acidified with 30% citric acid solution to pH 4, diluted with water and extracted five times with methylene chloride. The organic phase is washed three times with brine, dried on sodium sulfate and concentrarted by evaporation in a vacuum. The residue is purified by chromatography on silica gel. 0.85 g of the title compound as light pink oil is eluted with ethyl acetate/hexane mixtures.

IR (CHCl$_3$): 3021, 2960, 1740, 1665, 1624, 1446/cm.

The initial material for the above title compound is produced as follows:

(3a)

4-Cumyloxy-2-cyclopenten-1-one 6 ml of Jones reagent is instilled in a solution of 4.1 g of 4-cumyl-2-cyclopenten-1-ol (produced from cyclopentadiene according to S. Takano, Chem. Pharm. Bull. 34, 3445 (1986) in 50 ml of acetone at −30° C. and stirred for 20 minutes at −30° C. Then 6 ml of isopropanol is instilled, diluted with ether and shaken several times with water. It is dried with sodium sulfate and concentrated by evaporation in a vacuum. After filtering of the residue on silica gel with hexane/ethyl acetate mixtures, 3.81 g of 4-cumyloxy-2-cyclopenten-1-one is obtained as colorless oil.

I claim:

1. A process for the production of a bicyclo[3.3.0]octane dicarboxylic acid diester of general formula I,

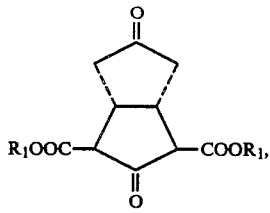

in which $R_1$ represents a straight-chain or branched-chain alkyl group with 1–10 C atoms, characterized in that a 2-cyclopentenone derivative of general formula III

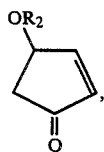

in which $R_2$ can be a hydrogen atom or a straight-chain or branched-chain alkyl group with 1–10 C atoms, which optionally can be substituted by a phenyl group, are reacted with an acetone dicarboxylic acid diester of formula IV,

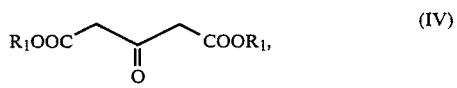

in which $R_1$ has the above-mentioned meaning, in the presence of a base.

2. A process according to claim 1, wherein $R_1$ is methyl, ethyl, propyl, isopropyl, n-butyl, isobutyl, tert-butyl, n-pentyl, isopentyl, neopentyl, n-hexyl, isohexyl, n-heptyl, isoheptyl, n-octyl, isooctyl, n-nonyl or n-decyl.

3. A process according to claim 1, wherein $R_2$ is substituted by a phenyl group.

4. A process according to claim 1, wherein the phenyl group is benzyl, phenethyl or cumyl.

5. A process according to claim 1, wherein the base is potassium carbonate, sodium carbonate, or a tertiary amine.

6. A process according to claim 1, wherein the process is carried out in the presence of a solvent.

7. A process according to claim 6, wherein the solvent is methanol, ethanol, isopropanol, methylene chloride or tetrahydrofuran or mixtures thereof.

8. A process according to claim 1, wherein the reaction is carried out at −60° C. to 60° C.

9. A process according to claim 8, wherein the process is carried out at 0° to 40° C.

* * * * *